United States Patent [19]
Burger

[11] Patent Number: 5,881,730
[45] Date of Patent: Mar. 16, 1999

[54] SURGICAL HAND SUPPORT APPARATUS

[76] Inventor: J. Lee Burger, Two E. Fortieth St., Paterson, N.J. 07154

[21] Appl. No.: 101,708

[22] Filed: Aug. 4, 1993

Related U.S. Application Data

[63] Continuation-in-part of Ser. No. 945,383, Sep. 16, 1992, Pat. No. 5,372,145.

[51] Int. Cl.$^6$ .................................................. A61F 5/37
[52] U.S. Cl. ........................... 128/878; 128/879; 602/20; 602/21
[58] Field of Search ............................. 5/623, 646, 647; 128/877, 878, 879; 378/180, 208; 602/5, 20, 21, 22

[56] References Cited

U.S. PATENT DOCUMENTS

| | | | |
|---|---|---|---|
| 2,266,230 | 12/1941 | Mazzeo et al. . | |
| 2,266,231 | 12/1941 | Mazzeo | 5/647 |
| 2,312,523 | 3/1943 | Corbett | 602/21 |
| 2,357,233 | 9/1944 | Goldberg | 128/84 |
| 2,863,449 | 12/1958 | Spencer | 602/21 |
| 3,476,108 | 11/1969 | Matukas | 128/133 |
| 3,540,719 | 11/1970 | Romney | 5/647 |
| 3,746,332 | 7/1973 | Hakstian | 5/647 |
| 3,762,401 | 10/1973 | Tupper | 128/879 |
| 3,901,227 | 8/1975 | Klatskin | 123/133 |
| 4,204,533 | 5/1980 | Forster | 128/879 |
| 4,252,306 | 2/1981 | Johnson et al. . | |
| 4,265,232 | 5/1981 | Stonich | 5/647 |
| 4,370,976 | 2/1983 | Wanchik et al. | 128/77 |
| 4,453,933 | 6/1984 | Speaker | 604/179 |
| 4,672,955 | 6/1987 | Cooper | 128/80 |
| 4,674,110 | 6/1987 | Eaton | 5/647 |
| 4,766,892 | 8/1988 | Kreitman . | |
| 4,909,264 | 3/1990 | Wadsworth, III et al. | 128/845 |
| 4,941,480 | 7/1990 | McLean et al. | 128/878 |
| 4,982,744 | 1/1991 | Stanec | 128/877 |
| 5,025,801 | 6/1991 | Callaway | 128/877 |
| 5,029,573 | 7/1991 | Chow . | |
| 5,136,742 | 8/1992 | Pirela-Cruz | 5/647 |
| 5,136,743 | 8/1992 | Pirela-Cruz | 128/878 |
| 5,140,998 | 8/1992 | Vickers | 128/879 |
| 5,279,574 | 1/1994 | Forren | 128/879 |

FOREIGN PATENT DOCUMENTS

| | | |
|---|---|---|
| 2088216 | 6/1982 | United Kingdom . |
| WO 8601711 | 3/1986 | WIPO . |
| WO 9406378 | 3/1994 | WIPO . |

*Primary Examiner*—Michael A. Brown

[57] ABSTRACT

A surgical hand support apparatus comprising a base block with a finger securing assembly comprising two uprights slidably mounted on tracks defined in the base block, a cross member connected to the uprights. A thumb securing assembly is also slidably mounted to the base block, the thumb securing assembly comprising a standard support member secured to the base block and a hook shaped rod mounted in the standard support member, the standard support member defining a slot through which a post extending from the side of the base block allowing the standard support member and associated hook shaped rod to be reciprocated for selective positioning around the thumb of the patient. A wrist securing assembly, is incorporated comprising a plurality of brackets slidably mounted to the base block and a cylindrical cross bar defining a plurality of instrument receiving holes is mounted to the uprights. A lock screw is connected to the cylindrical cross bar to lock the cross bar in place to secure the wrist of the patient and allow selective positioning of surgical instruments with respect to the hand.

28 Claims, 7 Drawing Sheets

SURGICAL HAND SUPPORT APPARATUS

RELATED CASES

This is a continuation-in-part of application Ser. No. 07/945,383 filed on Sept. 16, 1992, now U.S. Pat. No. 5,372,145.

BACKGROUND OF THE INVENTION

The present invention is directed towards a device for immobilizing a patient's hand while holding the hand on a specially constructed support board in order to facilitate various surgical procedures including endoscopy carpal tunnel release, percutaneous carpal tunnel-plasty and arthoscopy of the hand and wrist.

The human hand is the site of a large number of operative procedures and prior art hand restraints have not been able to fully immobilize the hand during a number of surgical procedures.

A number of restraint devices have been used to support and restrain a patient's hand for intravenous administration and various surgical procedures. U.S. Pat. No. 4,982,744 discloses an immobilizing apparatus including a composite sheet and arm board. The composite sheet includes an adhesive surface on one side and loop fastener on the other side. The arm board includes a fabric hook fastener which engages and holds the hook fasteners of the composite sheet. The patient's hand and/or forearm is secured to the composite sheet by placing the hand and/or forearm on the adhesive surface, the hooked surface of the composite sheet having been previously mounted to the hooked surface of the arm board. A hand belt constructed of fabric loop fasteners, can be used with the restraining device to immobilize the hand.

U.S. Pat. No. 5,140,998 discloses a surgical hand restrainer device with a flat mitt shaped base member, a spring finger trap and a slidable rigid thumb loop. The spring finger trap is in the form of a mouse trap type spring biased bar and it does not contain any wrist cross bars or guides for the insertion of instruments for performing any operative procedures inside the hand.

U.S. Pat. No. 3,762,401 discloses a paddle shaped base with a strap hand restraint. The wrist of the patient's hand is held by an optional wrist band and the individual fingers and thumb are held by elastic finger bands. The open wound is held open by a plurality of hooks mounted to a ball and link chain. The chains are mounted to the paddle base by inserting a link in one of a number of notches cut along the periphery of the paddle base.

U.S. Pat. No. 5,136,743 discloses an apparatus for positioning the distal radioulnar joint for medical examination and is constructed with a platform and a pair of upright blocks mounted on the platform in a spaced relationship to each other. Each of the blocks defines a plurality of slots which hold the posts of plexiglass stabilizing blocks. A post located near the forward end of the platform for selective insertion into anyone of a number of positioning holes cut into the platform provides a gripping surface by the subject.

U.S. Pat. No. 4,370,976 discloses a cast type device made of a soft resilient two piece hinged foam cast which closes together to hold the hand and forearm in a fixed position and is held together by straps.

U.S. Pat. No. 4,941,480 discloses a splint for immobilizing an patient's arm consisting of a three sided plastic foam support which is secured to the patient's arm with a series of VELCRO® straps.

U.S. Pat. Nos. 5,025,801; 4,909,264; 4,672,955; 4,453,933; 3,901,227; 3,476,108; 3,762,401; and 2,266,230, each disclose devices which temporarily restrain or support the hand and/or forearm using straps or bands to secure the hand for surgery or intravenous therapy. The use of straps is disadvantageous in that the straps are difficult to secure and also limit accessibility of the patient's hand and/or forearm.

SUMMARY OF THE INVENTION

In the present invention, the patient's hand is placed on an inclined plastic support base having a finger holding assembly and thumb securing assembly moveably mounted thereon for selective vertical and horizontal adjustment. The assemblies are secured to the support base by a moveable locking mechanism. The support base is inclined downward from the wrist assembly area towards the finger assembly. The inclined surface of the invention specifically allows instrumentation insertion into the carpal tunnel. A wrist holding assembly is mounted to the support base and is vertically adjustable thereon. The wrist assembly is provided with a cross bar allowing catheter guide instruments to be inserted therein for use in operating on the hand.

Thus, the present inventive device supports the hand and wrist comfortably for surgical procedures, particularly for minimally invasive hand surgery where instruments are inserted percutaneously or through very small incisions in the hand. The inventive device maximizes stability which decreases the fatigue of the surgeon's hands during delicate hand surgery. An assistant is not necessary because the inventive device secures the wrist, hand and fingers and is anatomically contoured for hand surgery with removable finger separators.

It is an object of the invention to provide a custom designed device for conventional hand surgery, endoscopic carpal tunnel release, percutaneous carpal tunnel plasty and arthoscopy of the hand and wrist. When performing percutaneous balloon carpal tunnel-plasty or endoscopic carpal tunnel release, the cross bar on the wrist securing assembly has a stop guide which protects the groove director guide from migrating downward. The stop guide when the balloon is inflated within the groove director allows the inflation of the balloon to only go superiorly, stretching and dilating the transverse carpal ligament. The underlying median nerve and other structures in the hand are protected throughout the procedure by this wrist securing assembly.

It is a further object of the invention to provide for a stop guide which facilitates the introduction of instruments such as grooved balloon guide protectors or an endoscope protecting underlying structures such as nerves, blood vessels and tendons while supporting the hand and wrist during surgical procedures including arthroscopy, carpal tunnel release, open reduction or fixation of fractures. The device is also radiolucent, facilitating interoperative radiograms for image intensification without moving the hand or wrist during surgery.

It is still another object of the invention to incorporate an optional finger trap device to maintain finger traction on the digits.

It is also an additional object of the invention to provide a device which is reusable, can be autoclaved, and is long lasting allowing the general handing of delicate tissues required of hand surgery.

In the accompanying drawings, there is shown an illustrative embodiment of the invention from which these and other of objectives, novel features and advantages will be readily apparent.

DETAILED DESCRIPTION OF THE INVENTION

The preferred embodiment and best mode of the invention is shown in FIGS. 1–9. The surgical hand support apparatus 10 is designed to hold a hand 200, wrist 201, thumb 202 and fingers 204 in a fixed position for surgery and image intensification.

The surgical hand support apparatus 10 is constructed with an inclined plastic base block 12 constructed of a radiolucent plastic material which can be autoclaved. The base block 12 has a planar base rim surface 14 with perpendicular side surfaces 15, front surface 16, rear surface 17 and an inclined hand support surface 18. The base rim surface 14 defines a hollow cavity (not shown) within the base block 12. The inclined hand support surface 18 is cut with an opposite slope of incline 19 from support surface 18 to allow the patient's wrist 201 to be bent backwards with the back of the wrist resting on sloped incline 19 allowing easy entrance of the surgical instrument. The inclined hand support surface 18 is inclined downward from the rear surface 17 to the front surface 16. The planar base surface 14 is provided with a plurality of support feet 13 which keep the block from slipping on the surface on which it is seated. The feet 13 are constructed of a material having a high coefficient of friction such as rubber or plastic.

Figure 1:
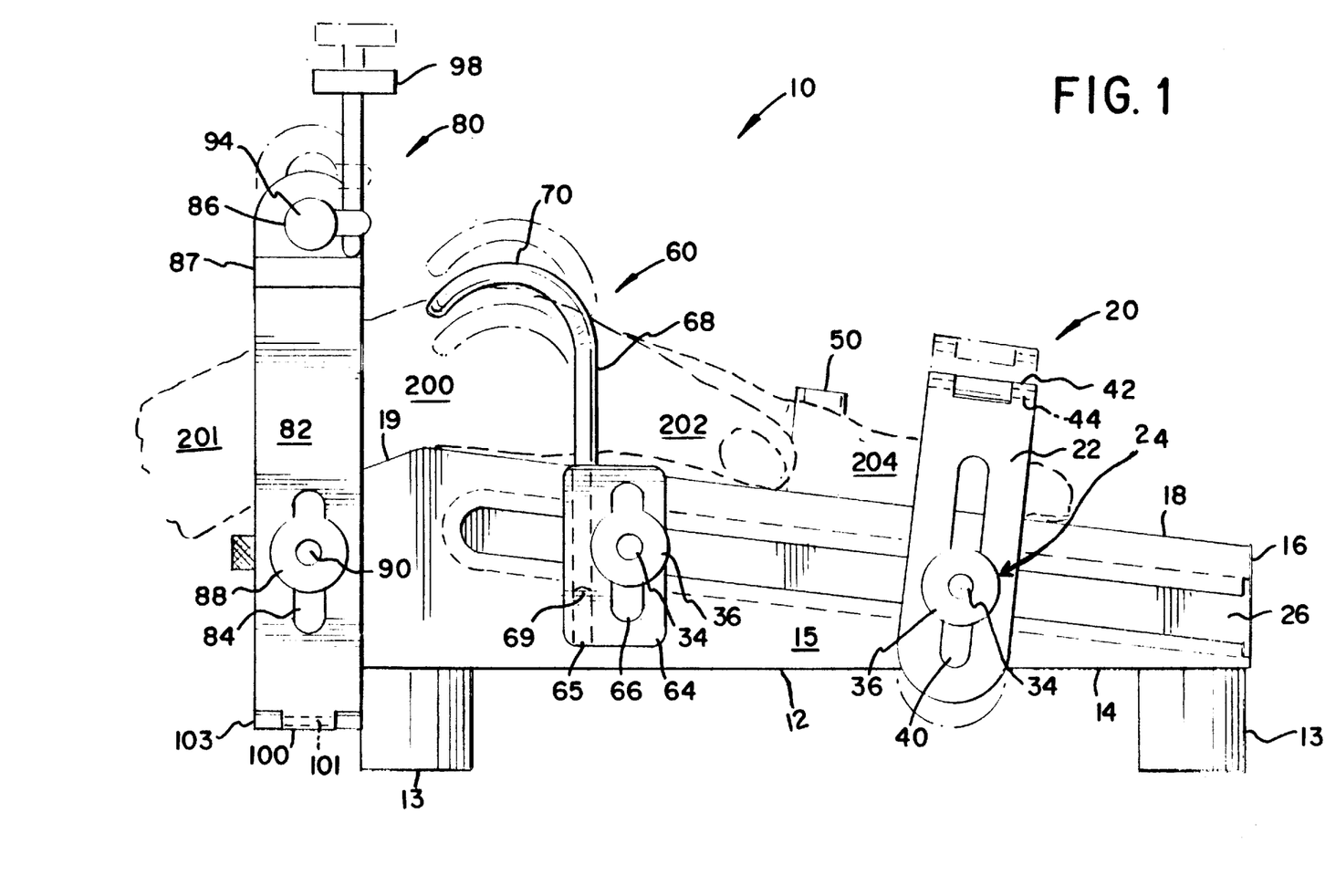
FIG. 1 is a side elevational view of the surgical hand support apparatus with an inserted patient's hand shown in phantom.
Figure 3:
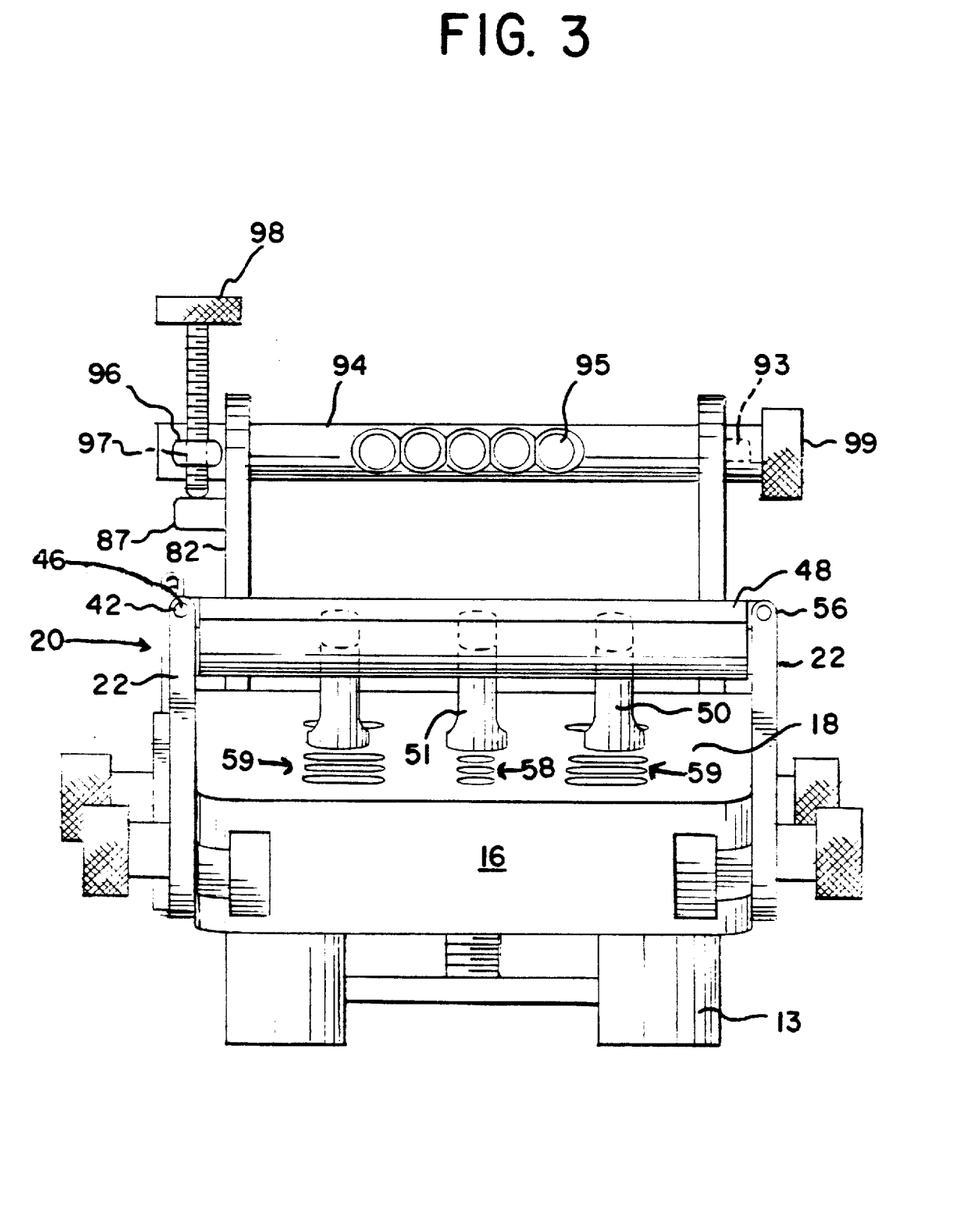
FIG. 3 is A front elevational view of the surgical hand support apparatus shown in FIG. 1.
Figure 4:
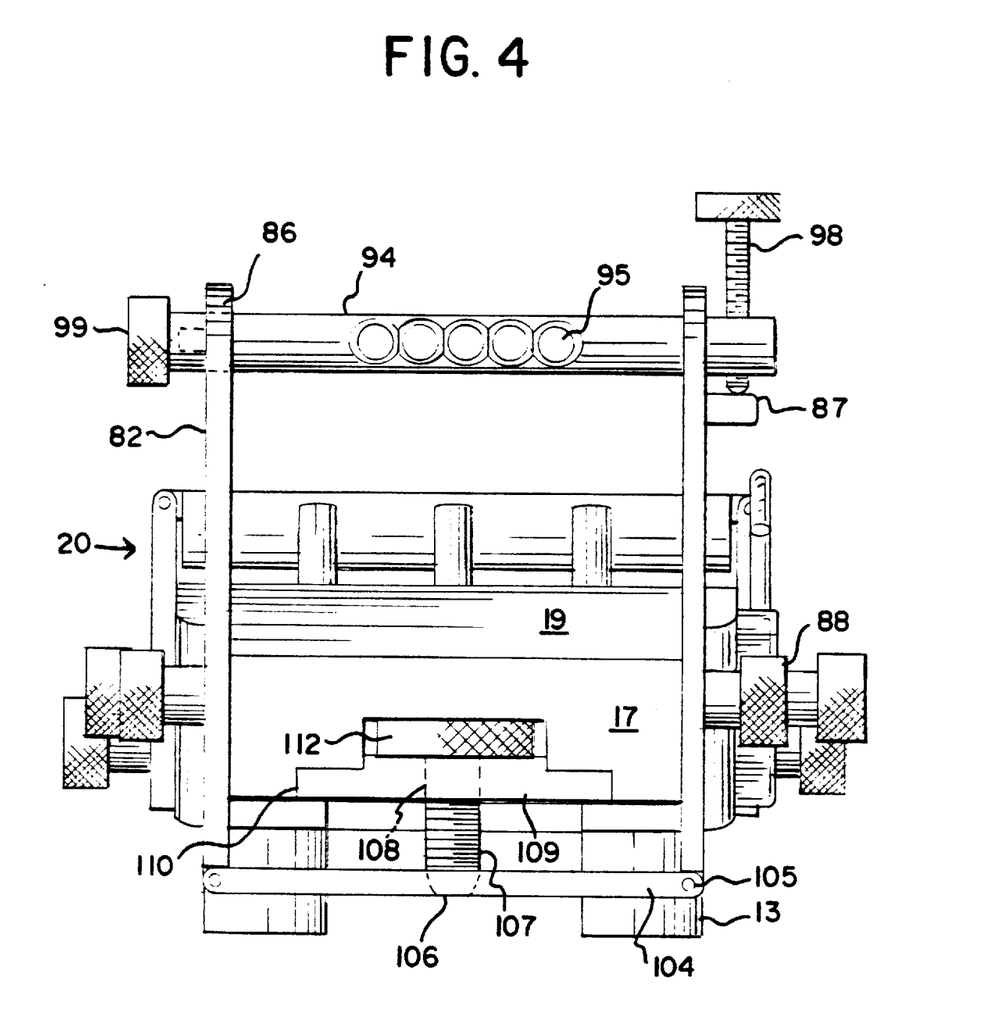
FIG. 4 is a rear elevational view of the surgical hand apparatus shown in FIG. 1.
Figure 5:
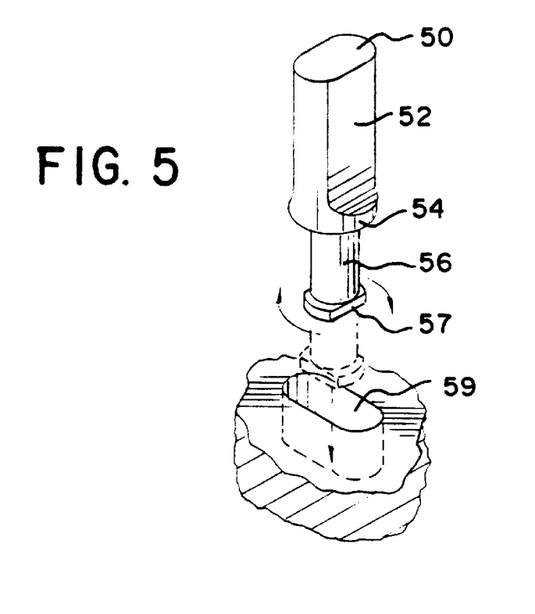
FIG. 5 is an exploded view partially in perspective showing the finger separator pins of the base block.
Figure 6:
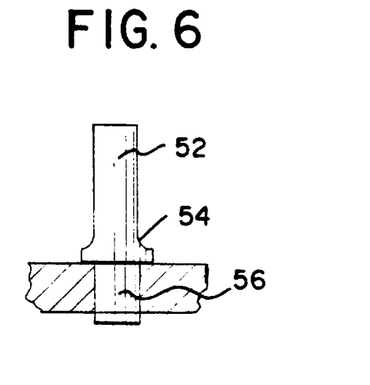
FIG. 6 is side elevation view of the finger separator pin as shown in FIG. 5 inserted into the base block.
Figure 7:
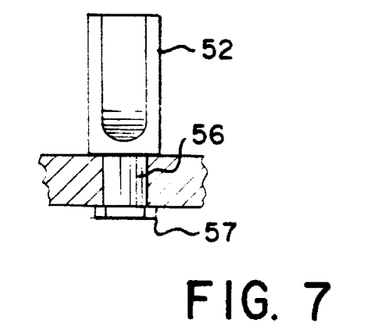
FIG. 7 is a sequential view of the finger separator pin inserted in the base block shown in FIG. 6 when the separator pin has been turned and locked into position.
Figures 8, 9:
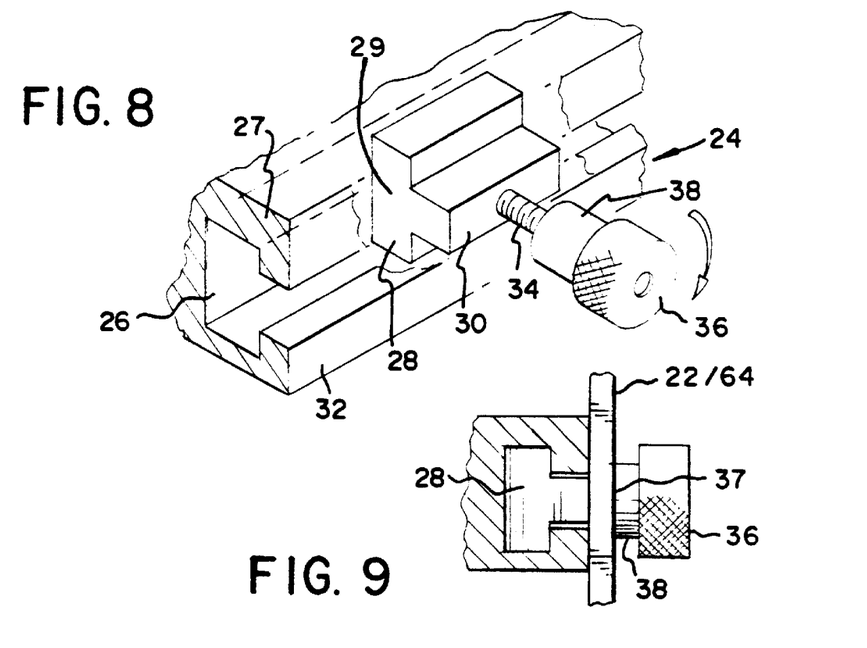
FIG. 8 is a partially cross sectional view of the track and slide guide mechanism mounted therein used to tighten the finger assembly and the thumb assembly with a portion of the base block removed.
FIG. 9 is a partial cross sectional end view taken along the track of FIG. 8 showing the slide guide mechanism and a section of upright locked into place on the base block.

The surgical hand support apparatus 10 is provided with a finger securing assembly 20 as shown in FIGS. 1, 2, 4 and 5 which incorporates a pair of stainless steel upright side members 22 which are secured to the base block 12 by slidable locking mechanisms 24 (FIG. 1). The locking mechanism 24 fits into a "T" shaped channel or track 26 formed by "C" shaped walls 27 of the base block as is most clearly seen in FIG. 8. Referring still to FIG. 8, a "T" shaped guide 28 is inserted into channel 26 opening at the front end 16 of the base block with the stem 29 of the "T" shaped guide extending outwardly with its planar base 30 following substantially the same plane as the outer surface of side wall 15 of the base block or being slightly recessed from the outer surface of the side wall. A threaded post 34 is secured to the "T" shaped guide member 28 and extends outward from the base 30 outside track 26 and past sidewall 15 of the base block. A knurled locking nut 36 provided with a stepped locking portion 38 is screwed onto the post 34 adjacent upright side members 22 allowing the finger securing assembly 20 and associated upright side member 22 to slide along the track or channel 26 cut into the base block. As shown in FIG. 1, the side members 22 are provided with slots 40 through which the post 34 of the locking mechanisms 24 projects. The top of the upright side members 22 are provided with arms 42 having an axially aligned bore 44 cut therethrough. The bore 44 receives the pin 46 as shown in FIG. 3. The pin 46 is also inserted through a throughgoing bore 47 cut through each end 49 (FIG. 2) of cross member 48. Cross member 48 is lowered by sliding upright side members 22 via slots 40 along a respective post 34 to engage the fingers 204 keeping them from moving up or down. The fingers 204 are separated and precluded from lateral movement through the use of finger separation pins 50 which are best shown in FIGS. 2, 3 and 5 through 7. Finger separating pins 50 are constructed with an oblong handle section 52 tapering to a stepped planar block engaging end 54. A circular post 56 extends from the block engaging end 54, the distal end of the post being provided with an oblong flanged locking section 57. The flange 57 and post 56 oriented as shown in phantom in FIG. 5 are inserted into throughgoing slot 59 cut through the base block 12 into the cavity. The handle 52 is then rotated turning the post and distal end so that the flanged locking section 57 is positioned perpendicular to the slot 59 as shown in FIGS. 5 and 7 keeping the finger pin 50 from being withdrawn. A separate finger separating pin 51 which has the configuration of the pin shown in FIG. 6, a circular post with no flange is placed in circular aperture 58 shown in FIG.3. This pin is easily removable and is put in after pins 50 have been locked into position to hold fingers 204 in a fixed lateral position. As noted, the construction of pin 51 is the same as pin 50 differing only in that pin 51 does not have flange 57.

As best shown in FIG. 3, there are three series of finger separating holes cut into the base block, two outside sets of oblong slots 59 and a center set of round holes 58. These holes provide maximum flexibility to stop or limit lateral movement of any size hand.

Figure 2:
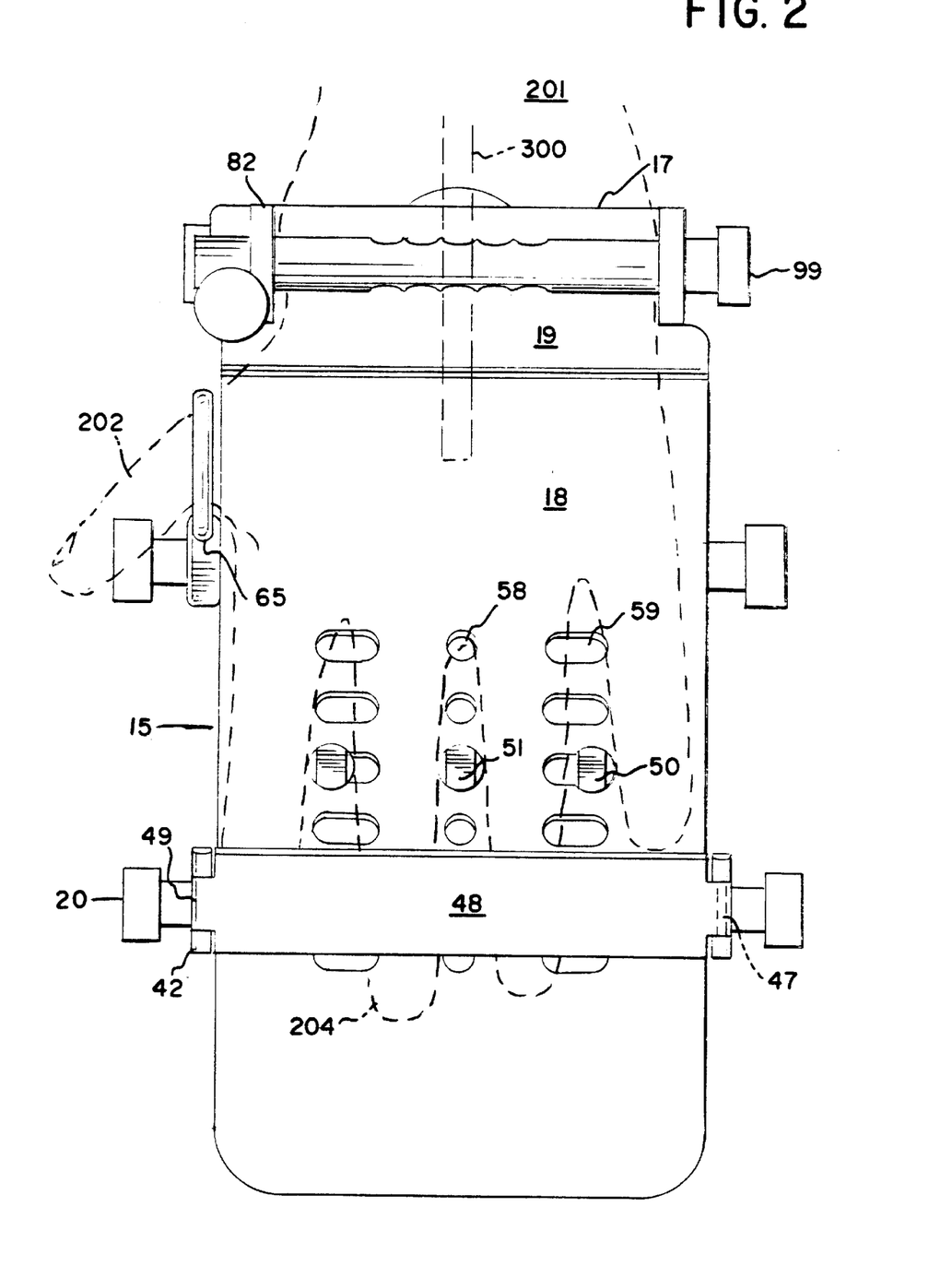
FIG. 2 is a top plan elevational view of the surgical hand support apparatus shown in FIG. 1 with the inserted patient's hand and guide director shown in phantom.

Referring now to FIG. 1,2 and 4, a thumb securing assembly 60 is slidably mounted to side 15 of base block 12 in the same manner as the finger assembly 20 to hold thumb 202 in place during surgery. The locking mechanism 24 is similar to the locking mechanism (FIG. 8) used in connection with the finger secured mechanism 20 and is constructed of a threaded side post 34 secured to base 30 of the "T" shaped guide 28. The side post 34 receives a knurled lock nut 36 with stepped locking portion 38 to hold a slidable support member 64 (FIG. 1) in a fixed position or can be unscrewed allowing the thumb assembly 60 to be moved to a selected position. The slidable support member 64 which has a rectangular configuration is provided with a slot 66 cut along its length which allows the side post 34 to be inserted therein allowing support member 64 to be selectively positioned by sliding it via slot 66 along side post 34 and along track or channel 26. The slidable support member 64 also defines a throughgoing bore 65 (shown in phantom in FIG. 1) which holds a curved thumb containment hook 68 in a fixed position. The thumb containment hook 68 is formed with a straight section 69 allowing the containment hook to be inserted in the throughgoing bore 65 with the other end of the thumb support hook being bent or curved at 70 which allows the curved end to be rotated over and around thumb 202. A knurled locking knob or nut 36 is threaded on the side post 34 to secure the slidable support member 64 causing the same to be held in a fixed position after the desired vertical placement of the curved thumb containment hook with relation to the thumb 202 is obtained.

A wrist holding assembly 80 as best shown in FIGS. 1, 3 and 4 is mounted to the base block 12. The wrist holding assembly is constructed with two upright brackets 82 mounted on each side of the base block, each bracket defining an adjustment slot 84 and a cross member aperture 86. One of the bracket uprights is provided with an integral locking seat 87 (FIG. 4) which extends outward perpendicular to the bracket surface. As shown in FIGS. 1 and 4 a locking knob 88 is mounted on threaded post 90. A threaded post 90 is secured in each side 15 of the base block 12 and extends through the adjustment slot 84 of upright bracket 82. The stepped locking end 89 of the locking knob 88 engages the outer surface of the upright bracket 82. The locking knob 88 is rotated, screwing the same on threaded post 90 so that stepped end 89 of the locking knob 88 abuts against the upright bracket 82, locking it into the desired vertical position against the base block 12. A cylindrical tool holder and wrist restrainer bar 94 is mounted through the apertures 86 in the upright brackets 82 and is supported by the upright brackets 82. The holder and wrist restrainer bar 94 defines a plurality of throughgoing bores 95 having a diameter sufficient to hold a catheter director or guide 300, which is shown in phantom in FIG. 2, and in perspective in FIG. 10, in the desired position for the surgery. The holder and wrist restrainer bar 94 also is provided on one end with a locking screw support nipple 96 (FIG. 3) having a threaded throughgoing bore 97 in which a locking screw 98 is threaded. The locking screw 98 is aligned so that it is adjacent the locking seat 87 and is screwed against the locking seat 87 keeping the bar 94 from rotating. The locking seat member 87 is screwed onto the upright bracket 82 with set screws which are recessed in throughgoing bores cut through the upright bracket 82 into threaded blind bores cut into the locking seat member 87. The other end of the holder bar 94 has a threaded post 93 which receives knurled limit end knob 99 to keep the holder bar from being pulled or slid out of the upright bracket 82. As shown in FIG. 1, the bottom end of each upright 82 is formed with a boss or end portion 100 having a throughgoing bore 101. As shown in FIGS. 1 and 4, the boss bore 101 is axially aligned with bores 102 cut in yoke arms 103 of a bottom cross member 104 to received holding pin 105 holding the bottom cross member 104 to the bottom of upright 102. The bottom cross member 104 has a throughgoing aperture 106 which receives the end and forms a seat for a threaded elevator screw 107. The elevator screw 107 is thus secured to bottom cross member 104 and extends into base block 12 adjacent rear wall 17. The elevator screw 107 which is fixed in place and does not turn holds a threaded insert 108 which is moveably mounted on the elevator screw and rotatably mounted in elevator block 109. The elevator block 109 is placed into a reverse "T" or hat shaped cut out 110 cut into the rear wall 17 of the base block 12 and is screwed to the base block with four set screws C (not shown) extending up through the rim into the base block. When the knurled handle 112 of insert 108 is rotated, the wrist holding assembly 80 and instrument guide cross member 94 moves or is driven vertically upward or downward to provide for vertical positioning of wrist holding assembly.

Figure 11:
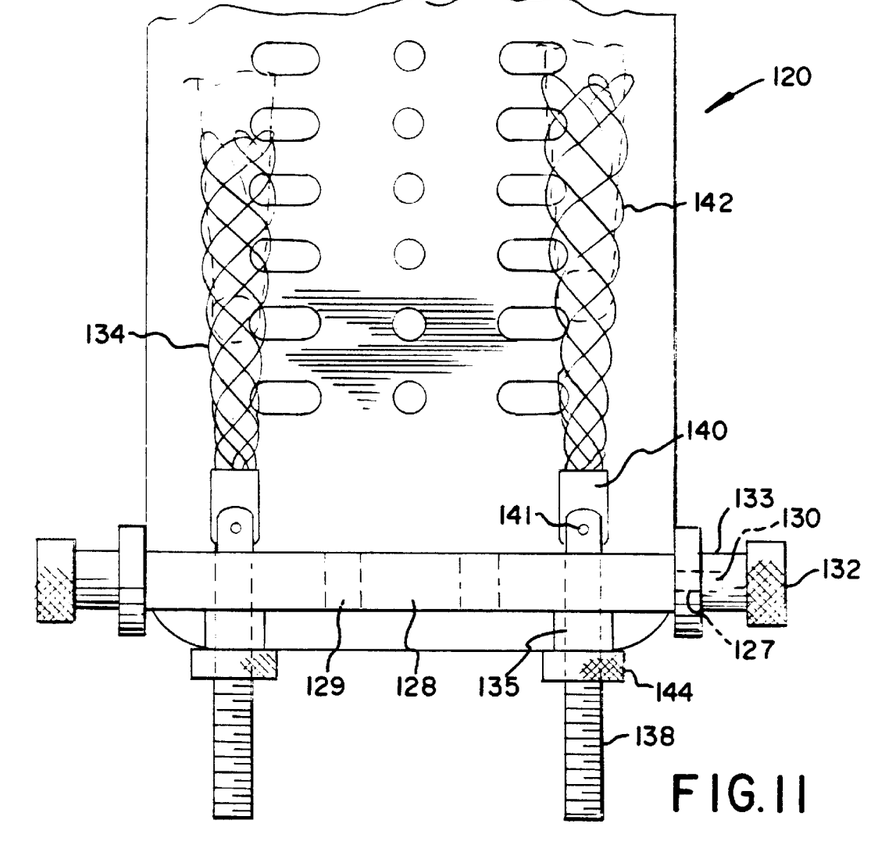
FIG. 11 is a alternate embodiment partial top plan view of the invention using a braided finger holder assembly with the patient's finger shown in phantom.
Figure 12:
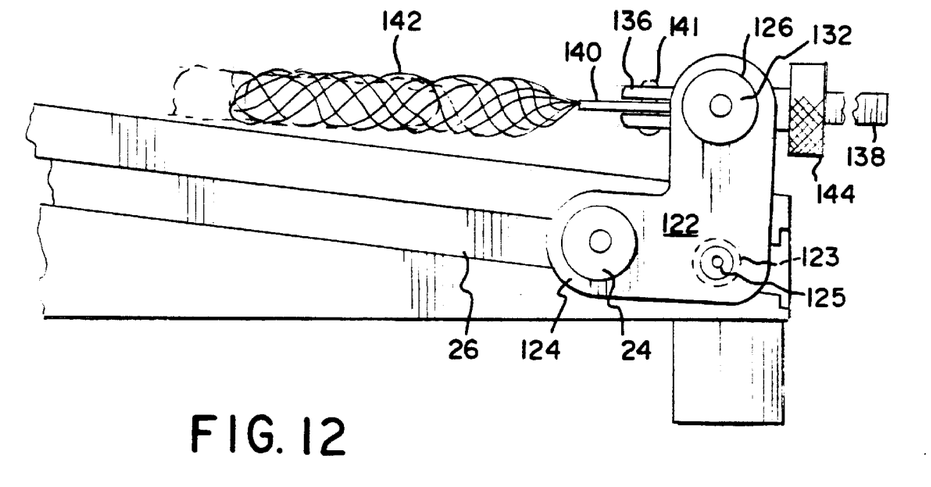
FIG. 12 is a side elevational view of the finger holding assembly embodiment shown in FIG. 11.

An alternative embodiment of the finger support assembly is shown in FIGS. 11 and 12. In this finger support assembly 120 "L" shaped standards 122 are slidably mounted in a track 26 via the guide mechanism 24 previously discussed and a secondary post 123 which screwed into the standard 122 by screw 125. One arm 124 of the "L" shaped standard holds the sliding and guide mechanism 24 and the other arm 126 holds a finger support bar 128 having an oblong cross section. The finger support bar 128 is provided with threaded posts 130 on each end which are inserted through a throughgoing bore 127 cut in arm 126 to receive a knurled stepped locking knob 132. The knurled locking knob has a stepped locking portion 133 which engages the outer surface of the "L" shaped standard when it is threaded onto the respective post 130. The finger support bar 128 is provided with a plurality of throughgoing bores 129 which can selectively hold one or more finger holding mechanisms 134. Each finger holding mechanism 134 is constructed with a circular post 135 having a yoke 136 at one end with the other end of post 138 being threaded. The yoke 136 holds a cup member 140 with a threaded pin 141, the cup member holding securely therein braided wire finger locks 142 commonly known as a Chinese finger locks. The finger locks 142 are compressed to receive a finger and allowed to expand after the finger is in place so that attempted removal of the finger results in stretching thus holding the finger in the finger lock. The threaded post end 138 has a knurled driving nut 144 which engages the rear surface of the finger support bar 128 allowing the finger locks 142 to be transported laterally with respect to the top surface of the inclined block. Thus, the patient's fingers 204 are inserted into the finger locks 142 so that the respective finger 204 is inserted up into the compressed braided wire finger lock 142 at which time the compressed braided wire is relaxed and allowed to expand tightly holding the fingers. When the wrist restraint assembly 80 is placed in position, the fingers 204 are held in a locked position and the finger locks 142 can be tightened or loosened by movement of the locking nut 144 driving the finger locks 142 toward or away from the patient, thus, keeping the patient's fingers in a selected tensional fixed position.

When the device 10 is being used in an operation, the patient's hand 200 is laid on the inclined surface 18 of block 12 with the fingers 204 placed on the lower part of inclined surface 18 and the wrist on the upper part of the inclined surface 18 projecting downward on slope 19. The finger support bar 48 and connected upright side members 22 are then slid along tracks 26 cut into the base block 12 via locking mechanism 24 and its associated guide 28 until the bar 48 is positioned over the fingers 204. The finger support bar 48 is then slid downward along slots 40 in upright side support members 22 until it engages fingers 204. Tensioning knobs 36 are rotated on each respective center post 34 until the planar base 37 of the stepped portion 38 engages the outer surface of the upright side member 22 locking the finger securing assembly 20 into a fixed position on the block 12 engaging the finger 204. Pins 50 have been previously mounted and locked in holes 59 of the base block to limit lateral movement of the fingers and middle pin 51 is inserted into aperture 58 the base block 12. The thumb assembly 60 is then engaged with the patient's thumb 202 by sliding the hook member 68 and its associated support member 64 upward, and sliding support member 64 downward until the bottom of hook 68 engages the thumb 202 holding it against the surface 18 of block 12. The locking knob 36 is then rotated to hold the support member 64 and thumb hook 68 in a fixed position.

Figure 10:
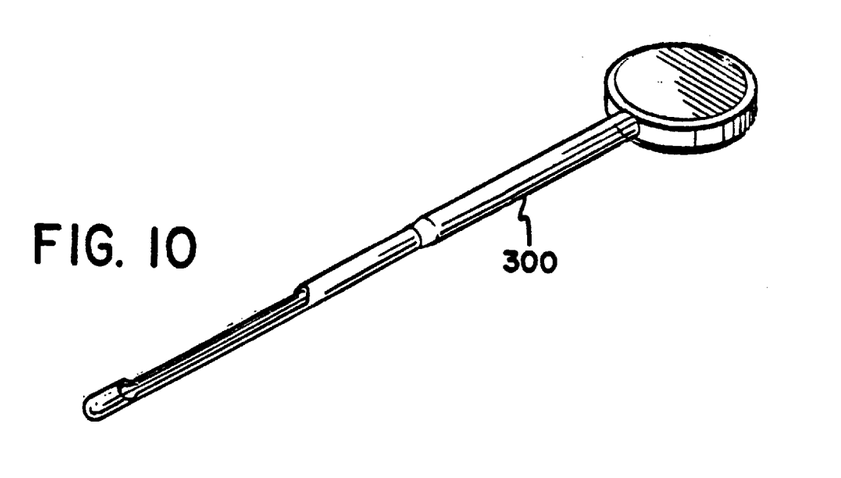
FIG. 10 is a perspective view of a catheter guide instrument used in the wrist holding assembly.

The wrist restraining bar 94 is then inserted through bores 86 in the bracket uprights 82 and the limit knob 99 is screwed into the end of the wrist restraining bar. Adjustments can be made by turning the elevator adjustment knob 112 which raises and lowers the wrist holding assembly 80 in relation to inclined surface 18 until the wrist restraining bar 94 engages the wrist. The bracket uprights 82 are then locked into position by screwing locking knobs 88 into threaded post 90 so that the stepped end 89 of locking knob 88 abuts against the external surface of bracket upright 82 holding it in a fixed position against block 12. Locking screw 98 is screwed into locking seat 87 holding the restraining bar 94 in fixed position for insertion of surgical instruments. Necessary surgical instruments such as guides 300 as shown in FIG. 10 can be inserted through bores 95 against the hand 202 at which time surgery commences.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A surgical hand support apparatus, comprising:
   a base block including a supporting surface upon which a patient's hand is supported;
   a finger securing assembly movably mounted to the base block, including:
      a plurality of upright members slidably mounted to the base block for selective positioning along both a horizontal and a vertical axis; and
      a cross post mounted to the upright members to engage and retain the patient's fingers against the supporting surface; and
   a movable wrist securing assembly mounted to the base block to engage and retain the patient's wrist against the supporting surface.

2. The apparatus as claimed in claim 1 further including a plurality of removable pin members selectively mounted in a plurality of bores defined in the base block, the pin members extending from the supporting surface to separate and limit movement of the patient's fingers.

3. The apparatus as claimed in claim 1 wherein the wrist securing assembly comprises a plurality of bracket members, a cross bar mounted in said bracket members and locking means connected to said cross bar to lock said cross bar in a fixed position.

4. The apparatus as claimed in claim 3 wherein the cross bar defines a plurality of apertures formed therein, each aperture dimensioned to permit insertion of an instrument therethrough.

5. The apparatus as claimed in claim 1 further comprising means for retaining the finger securing assembly in a fixed position relative to the longitudinal and the vertical axis.

6. A surgical hand support apparatus comprising:
   a base block for supporting a patient's hand and defining an X-axis and a Y-axis;
   a finger securing mechanism movably mounted to the base block for selective positioning along the X axis and the Y axis, the finger securing mechanism including:
      a plurality of uprights movably mounted to the base block; and
      a cross member mounted to the uprights to retain the patient's fingers against the base block;
   a thumb securing mechanism movably mounted to the base block, including:
      a standard member movably mounted to the base block and having a curved rod member secured thereto; and
      fastening means associated with the base block for permitting the standard member to be moved to a selected position along the X axis and the Y axis and fastened in a fixed position; and
   a wrist securing mechanism mounted to the base block, including:
      a plurality of bracket members;
      a cross bar mounted to the bracket members; and
      elevator means connected to the bracket members to move the bracket members and associated cross bar along the Y axis to a selected position.

7. The apparatus as claimed in claim 6 wherein the base block includes an inclined surface portion upon which the patient's hand is supported.

8. The apparatus as claimed in claim 6 wherein the bracket members of the wrist securing mechanism each include a cross bar aperture for reception of the cross bar and a slot extending along the Y-axis, the wrist securing mechanism further including lock means for selectively locking the bracket members at a selected position along the Y-axis, the lock means including a threaded shaft extending from the base block and received within the slot of the bracket member and a threaded locking knob mounted on the threaded shaft.

9. An apparatus as claimed in claim 6 wherein the base block includes at least one track extending along the X-axis.

10. The apparatus as claimed in claim 9 wherein the fastening means of the thumb securing mechanism comprises a guide member mounted in the track formed in the base block, a threaded post extending outwardly from the guide member and received within a slot in the standard member and a locking knob threaded on the threaded post.

11. A surgical hand support apparatus comprising:
    a base block defining a longitudinal axis, and having an inclined upper surface adapted to support a patient's hand, the base block defining first and second generally longitudinally extending tracks;
    a finger securing assembly mounted to the base block, including:
       first and second upright members slidably mounted in the first and second tracks; and
       a cross member mounted to the first and second upright members, the cross member positionable to engage the patient's fingers;
    a thumb securing mechanism mounted to the base block and movable to engage the patient's thumb; and
    a rigid wrist securing assembly mounted to the base block to selectively assume a desired position with respect to the upper surface of the base block to engage the patient's wrist.

12. The apparatus as claimed in claim 11 further comprising at least two spaced pin members extending from the base block, each pin member positionable between adjacent fingers of the patient's hand to separate the adjacent fingers and limit lateral movement thereof.

13. The apparatus as claimed in claim 12 comprising three pin members, the three pin members including a centrally disposed pin member and first and second outer pin members.

14. The apparatus as claimed in claim 13 wherein the base block includes three series of apertures formed therein, a first of the series dimensioned to accommodate the centrally disposed pin member, a second and a third of the series dimensioned to accommodate the first and second outer pin members.

15. The apparatus as claimed in claim 11 further comprising a finger holding mechanism associated with the cross-bar for maintaining the patient's fingers in spaced relation.

16. The apparatus as claimed in claim 15 wherein the finger holding mechanism includes at least two braided wire finger locks connected to the cross bar, each finger lock engageable with one of the patient's fingers and adapted to securely hold the one finger in a fixed position.

17. A surgical hand support apparatus to assist in a surgical operation, which comprises:
   a) a base member including a supporting surface for supporting a patient's hand in a prostrate position with the palm of the patient's hand facing away from the supporting surface, the base member defining a longitudinal axis; and
   b) a finger securing assembly mounted to the base member, the finger securing assembly including a cross bar for engaging the patient's fingers and for retaining the fingers against the supporting surface, the cross bar positioned in superposed relation relative to the base member and being moveable in a first direction having a longitudinal component relative to the longitudinal axis such that the cross bar is selectively positionable at a plurality of predetermined longitudinal positions, the cross bar being movable in a second direction having a transverse component relative to the longitudinal axis such that the cross bar is selectively positionable at a plurality of predetermined lateral positions.

18. The surgical hand support apparatus of claim 17 further including means for securing the cross bar of the finger securing assembly at each of the plurality of predetermined longitudinal positions.

19. The surgical hand support apparatus of claim 17 further including means for securing the cross bar of the finger securing assembly at a selected lateral position relative to the supporting surface.

20. The surgical hand support apparatus of claim 17 further including a wrist securing assembly mounted to the base member, the wrist securing assembly including an engaging member for engaging the patient's wrist and for retaining the wrist against the supporting surface.

21. The surgical hand support apparatus of claim 20 further including a thumb securing assembly mounted to the base member, the thumb securing assembly including an engaging member for engaging the patient's thumb and for retaining the thumb against the supporting surface.

22. The surgical hand support apparatus of claim 17 further including a thumb securing assembly mounted to the base member, the thumb securing assembly including an engaging member for engaging the patient's thumb and for retaining the thumb against the supporting surface.

23. The surgical hand support apparatus of claim 17 including at least two members mounted to and extending from the supporting surfaces, each member positionable between adjacent fingers of the patient's hand to separate the adjacent fingers and minimize movement thereof.

24. A surgical hand support apparatus to assist in a surgical operation, which comprises:
   a) a base member including a supporting surface for supporting a patient's hand and defining a longitudinal axis; and
   b) a thumb securing assembly mounted to the base member, the thumb securing assembly including a relatively rigid engaging member for engaging the patient's thumb and for retaining the thumb against the supporting surface, the thumb securing assembly being moveable in a first direction having a longitudinal component relative to the longitudinal axis such that the engaging member is selectively positionable at a plurality of predetermined longitudinal positions and laterally moveable in a second direction having a transverse component relative to the longitudinal axis such that the engaging member is selectively positionable at a plurality of predetermined lateral positions.

25. The surgical hand support apparatus of claim 24 further including means for securing the thumb securing assembly at each of the predetermined longitudinal positions.

26. The surgical hand support apparatus of claim 24 further including means for securing the engaging member of the thumb securing assembly at a predetermined lateral position above the supporting surface.

27. The surgical hand support apparatus of claim 24 further including a wrist securing assembly mounted to the base member, the wrist securing assembly including an engaging member for engaging the patient's wrist and for retaining the wrist against the support surface.

28. A surgical hand support apparatus to assist in a surgical operation, which comprises:
   a) a base member defining a supporting surface for supporting a patient's hand and wrist; and
   b) a cross member extending across the supporting surface and being supported by a bracket member, one of the cross member and the bracket member moveable in a lateral direction relative to the supporting surface such that the cross member engages the patient's wrist to retain the patient's wrist thereagainst, the cross member including at least one aperture therethrough dimensioned for reception of a surgical instrument to support the instrument during the surgical operation.

* * * * *